United States Patent [19]

Takei et al.

[11] Patent Number: 5,648,457
[45] Date of Patent: Jul. 15, 1997

[54] PURIFICATION METHOD FOR HYDROPHOBIC POLYPEPTIDE

[75] Inventors: Tsunetomo Takei; Toshimitsu Aiba; Kaoru Sakai, all of Tokyo; Tetsuro Fujiwara, Morioka, all of Japan

[73] Assignee: Tokyo Tanabe Company Limited, Tokyo, Japan

[21] Appl. No.: 343,427

[22] Filed: Nov. 21, 1994

[30] Foreign Application Priority Data

Apr. 30, 1993 [JP] Japan ................... 5-103957

[51] Int. Cl.$^6$ ............... C07K 14/00; C07K 1/16
[52] U.S. Cl. ............ 530/324; 530/344; 530/412
[58] Field of Search ................... 530/324, 414, 530/344, 361, 412

[56] References Cited

U.S. PATENT DOCUMENTS 4,894,330  1/1990  Hershenson et al. ............ 435/69.51

FOREIGN PATENT DOCUMENTS 1-501282  5/1989  Japan.
3-78371  12/1991  Japan.
4-98083  10/1993  Japan.

*Primary Examiner*—Cecilia J. Tsang
*Assistant Examiner*—Anism Gupta
*Attorney, Agent, or Firm*—McGlew & Tuttle

[57] ABSTRACT

The present invention is directed to a purification method for hydrophobic polypeptides by using high performance liquid chromatography, characterized by using a mixed solvent as a moving phase, in which the portion of trifluoroacetic acid is from 3 to 10% by volume, and polyvinyl alcohol-based column filler in the said high performance liquid chromatography. The method according to the present invention is useful as a purification method for hydrophobic polypeptides in view of the fact that the pulmonary surfactant, which is prepared from the hydrophobic polypeptide purified according to the method of the present invention, shows better surface active property than the hydrophobic polypeptides purified by customary methods for the purification.

28 Claims, No Drawings

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 27 amino acids
        ( B ) TYPE: Amino acid
        ( C ) TOPOLOGY: Linear ( i i ) MOLECULE TYPE: Peptide ( x i ) SEQUENCE DESCRIPTION: SEQ ID NO: 1:

```
Cys Pro Val His Leu Lys Arg Leu Leu Ile Val Val Val Val Val
1               5                   10                  15

Leu Ile Val Val Val Ile Val Gly Ala Leu Leu
                20              25
```

( 2 ) INFORMATION FOR SEQ ID NO:2:

( i ) SEQUENCE CHARACTERISTICS:
        ( A ) LENGTH: 27 amino acids
        ( B ) TYPE: Amino acid
        ( C ) TOPOLOGY: Linear ( i i ) MOLECULE TYPE: Peptide ( x i ) SEQUENCE DESCRIPTION: SEQ ID NO: 2:

```
Cys Cys Pro Val His Leu Lys Arg Leu Leu Ile Val Val Val Val
1               5                   10                  15

Val Leu Ile Val Val Val Ile Val Gly Ala Leu
                20              25
```

( 2 ) INFORMATION FOR SEQ ID NO:3:

( i ) SEQUENCE CHARACTERISTICS:
        ( A ) LENGTH: 27 amino acids
        ( B ) TYPE: Amino acid
        ( C ) TOPOLOGY: Linear ( i i ) MOLECULE TYPE: Peptide ( x i ) SEQUENCE DESCRIPTION: SEQ ID NO: 3:

```
Cys Pro Val Asn Ile Lys Arg Leu Leu Ile Val Val Val Val Val
1               5                   10                  15

Leu Leu Val Val Val Ile Val Gly Ala Leu Leu
                20              25
```

( 2 ) INFORMATION FOR SEQ ID NO:4:

( i ) SEQUENCE CHARACTERISTICS:
        ( A ) LENGTH: 27 amino acids
        ( B ) TYPE: Amino acid
        ( C ) TOPOLOGY: Linear ( i i ) MOLECULE TYPE: Peptide ( x i ) SEQUENCE DESCRIPTION: SEQ ID NO: 4:

```
Cys Cys Pro Val Asn Ile Lys Arg Leu Leu Ile Val Val Val Val
1               5                   10                  15

Val Leu Leu Val Val Val Ile Val Gly Ala Leu
                20              25
```

( 2 ) INFORMATION FOR SEQ ID NO:5:

( i ) SEQUENCE CHARACTERISTICS:
    ( A ) LENGTH: 27 amino acids
    ( B ) TYPE: Amino acid
    ( C ) TOPOLOGY: Linear ( i i ) MOLECULE TYPE: Peptide ( x i ) SEQUENCE DESCRIPTION: SEQ ID NO: 5:

Cys Pro Val Asn Leu Lys Arg Leu Leu Val Val Val Val Val Val
1               5                   10                  15

Leu Val Val Val Val Ile Val Gly Ala Leu Leu
            20                  25

( 2 ) INFORMATION FOR SEQ ID NO:6:

( i ) SEQUENCE CHARACTERISTICS:
    ( A ) LENGTH: 27 amino acids
    ( B ) TYPE: Amino acid
    ( C ) TOPOLOGY: Linear ( i i ) MOLECULE TYPE: Peptide ( x i ) SEQUENCE DESCRIPTION: SEQ ID NO: 6:

Cys Cys Pro Val Asn Leu Lys Arg Leu Leu Val Val Val Val Val Val
1               5                   10                  15

Val Leu Val Val Val Val Ile Val Gly Ala Leu
            20                  25

( 2 ) INFORMATION FOR SEQ ID NO:7:

( i ) SEQUENCE CHARACTERISTICS:
    ( A ) LENGTH: 27 amino acids
    ( B ) TYPE: Amino acid
    ( C ) TOPOLOGY: Linear ( i i ) MOLECULE TYPE: Peptide ( x i ) SEQUENCE DESCRIPTION: SEQ ID NO: 7:

Ser Pro Val His Leu Lys Arg Leu Leu Ile Val Val Val Val Val
1               5                   10                  15

Leu Ile Val Val Val Ile Val Gly Ala Leu Leu
            20                  25

( 2 ) INFORMATION FOR SEQ ID NO:8:

( i ) SEQUENCE CHARACTERISTICS:
    ( A ) LENGTH: 27 amino acids
    ( B ) TYPE: Amino acid
    ( C ) TOPOLOGY: Linear ( i i ) MOLECULE TYPE: Peptide ( x i ) SEQUENCE DESCRIPTION: SEQ ID NO: 8:

Ser Ser Pro Val His Leu Lys Arg Leu Leu Ile Val Val Val Val Val
1               5                   10                  15

Val Leu Ile Val Val Val Ile Val Gly Ala Leu
            20                  25

( 2 ) INFORMATION FOR SEQ ID NO:9:

( i ) SEQUENCE CHARACTERISTICS:
    ( A ) LENGTH: 27 amino acids
    ( B ) TYPE: Amino acid
    ( C ) TOPOLOGY: Linear ( i i ) MOLECULE TYPE: Peptide ( x i ) SEQUENCE DESCRIPTION: SEQ ID NO: 9:

```
Ala  Pro  Val  His  Leu  Lys  Arg  Leu  Leu  Ile  Val  Val  Val  Val  Val
1                   5                        10                       15
Leu  Ile  Val  Val  Val  Ile  Val  Gly  Ala  Leu  Leu
                    20                   25
```

( 2 ) INFORMATION FOR SEQ ID NO:10:

( i ) SEQUENCE CHARACTERISTICS:
        ( A ) LENGTH: 27 amino acids
        ( B ) TYPE: Amino acid
        ( C ) TOPOLOGY: Linear ( i i ) MOLECULE TYPE: Peptide ( x i ) SEQUENCE DESCRIPTION: SEQ ID NO: 10:

```
Ala  Ala  Pro  Val  His  Leu  Lys  Arg  Leu  Leu  Ile  Val  Val  Val  Val
1                        5                        10                       15
Val  Leu  Ile  Val  Val  Val  Ile  Val  Gly  Ala  Leu
                    20                   25
```

( 2 ) INFORMATION FOR SEQ ID NO:11:

( i ) SEQUENCE CHARACTERISTICS:
        ( A ) LENGTH: 35 amino acids
        ( B ) TYPE: Amino acid
        ( C ) TOPOLOGY: Linear ( i i ) MOLECULE TYPE: Peptide ( x i ) SEQUENCE DESCRIPTION: SEQ ID NO: 11:

```
Phe  Gly  Ile  Pro  Cys  Cys  Pro  Val  His  Leu  Lys  Arg  Leu  Leu  Ile  Val
1                   5                        10                       15
Val  Val  Val  Val  Val  Leu  Ile  Val  Val  Val  Ile  Val  Gly  Ala  Leu  Leu
                    20                        25                                32
Met  Gly  Leu
          35
```

PURIFICATION METHOD FOR HYDROPHOBIC POLYPEPTIDE

This application is a 371 of PCT/JP94/00731, filed Apr. 28, 1994.

1. Technical Field of the Invention

The present invention relates to a purification method for hydrophobic polypeptide, and more particularly to a purification method for hydrophobic polypeptide which shows more intensive surface activity by means of combining said polypeptide with lipid mixture.

2. Background Art

Infantile respiratory distress syndrome is a disease which induces serious respiratory disorder as a result of the collapse of lung due to the deficiency of pulmonary surfactant and is observed in premature newborns with high mortality. In recent years, for the treatment of this respiratory distress syndrome, a supplemental therapy in which pulmonary surfactant is administrated via transairway route from the outside has developed, and this therapy has demonstrated successful results.

Some of the inventors of the present invention isolated lipoprotein from pulmonary surfactant derived from animals, and they have found that the lipoprotein is an essential component for showing pulmonary surface activity, and that pulmonary surfactant as the complex of lipid-lipoprotein mixture prepared by combining said lipoprotein with lipid mixture enabled the demonstrating of excellent surface activity, namely the activity for lowering surface tension, and the securing of alveolar space volume sufficient to maintain normal respiratory function by demonstrating the shortening of niveau surface spreading time and low equilibrium surface tension, thereby allowing the utilizing of the lipoprotein for the treatment of respiratory distress syndrome (See Japanese Patent Publication No. Hei 3-78371 Gazette).

Furthermore, the inventors of the present invention found that a synthesized polypeptide having a partial structure of apoprotein C (sequence number 11, hereinafter referred to as "SP-C"), which is a specific apoprotein to pulmonary surface from mammals shows strong surface activity when it is combined with lipid mixture (Japanese Patent Application No. Hei 4-98083).

However, purification of SP-C and the synthesized polypeptide described above having partial structure of SP-C was so difficult due to extremely low solubility of said polypeptide to the moving phase, which is based on very high hydrophobic property of them when it is treated in the condition of normal high-performance liquid chromatography (hereinafter referred to as "HPLC").

In general, hydrophobic protein or polypeptide is defined as the one having relatively high content of hydrophobic amino acid including isoleucine, tyrosine, phenylalanine, leucine, valine and methionine among the component amino acid residue of protein or polypeptide. In Table 1, the number of total amino acid residues as to main protein, the number of hydrophobic amino acid residues and the content of hydrophobic amino acid (number of hydrophobic amino acid residues/number of total amino acid residues, and so forth) were shown. As can be seen from the table, it is shown that both surfactant apoprotein B (hereinafter referred to as "SP-B") and SP-C are respectively a highly-hydrophobic protein compared to the other proteins, i.e. each is a hydrophobic polypeptide having a hydrophobic amino acid content of more than 50% compared to the other proteins wherein such content is clearly less than 50%.

TABLE 1

| Protein | Number of total Amino Acid | Number of Hydrophobic Amino Acid | Content of Hydrophobic Amino Acid (%) |
|---|---|---|---|
| Glutamic dehydrogenase (Bovine, liver) | 500 | 199 | 39.8 |
| Aldolase A-Chain (Rabbit, myocardium) | 361 | 148 | 41.0 |
| Lysozyme (Chicken, albumin) | 129 | 45 | 34.9 |
| Trypsine (Bovine, spleen) | 229 | 77 | 33.6 |
| Pepsin (Porcine) | 327 | 128 | 39.1 |
| Basic Trypsinse Inhibitor (Bovine, spleen) | 58 | 20 | 34.5 |
| Insulin A, B-Chain (Human) | 41 | 17 | 41.5 |
| Glucagon (Human) | 29 | 8 | 27.6 |
| Calcitonin (Human) | 32 | 12 | 37.5 |
| HDL-apoA-I (Human) | 245 | 94 | 38.4 |
| HDL-apoA-II (Human) | 77 | 29 | 37.7 |
| Myosin A1 L-Chain (Rabbit, skeletal muscle) | 190 | 84 | 44.2 |
| κ-casein B Variant (Bovine, milk) | 169 | 74 | 43.8 |
| Serum Albumin (Human) | 585 | 234 | 40.0 |
| Basic Protein (Human, myelin membrane) | 171 | 53 | 31.0 |
| SP-B | 57 | 36 | 63.2 |
| SP-C | 35 | 27 | 77.1 |

For purification of such hydrophobic polypeptides, a method using reversed-phase HPLC which uses polar solvent, such as $H_2O$, acetonitrile and methanol as moving phase, has been widely adopted.

For the moving phase, an example of reversed-phase HPLC using a mixed solvent obtained by adding an organic acid, such as formic acid and trifluoroacetic acid to a polar solvent, such as $H_2O$, acetonitrile and methanol is known; however, the concentration of trifluoroacetic acid used therein, for example, is a trace amount as small as 0.5% (Japanese Patent Laid-open No. Hei 1-501282 Gazette).

On the other hand, an attempt to perform reversed-phase HPLC for purifying hydrophobic proteins, such as SP-B and SP-C, which are contained in pulmonary surface active agent derived from animals by using an aforementioned solvent as a moving phase was difficult to carry out because of low solubility of said hydrophobic protein in the moving phase.

Moreover, it was not possible to avoid the contamination of a trace amount of impurity into the hydrophobic polypeptide synthesized, even though it is applied for HPLC containing polyvinyl alcohol-based column filler and using the aforementioned polar solvents as the moving phase. If such a contaminant exists, the pulmonary surfactant is colored, and the hydrophobic polypeptide unables to demonstrate sufficient surface activity since it causes polymerization of itself arising from the coagulation of itself.

Under the circumstances as described above, it has been urgently required to develop an improved purification method.

DISCLOSURE OF THE INVENTION

Based upon the knowledge as described above, the inventors of the present invention have intensively investigated the finding of a method for purifying hydrophobic polypeptides, and then they found an excellent purifying method wherein the hydrophobic polypeptide is dissolved in trifluoroacetic acid (hereinafter referred to as "TFA") and is applied to HPLC in which a mixed solvent containing TFA is used as a moving phase and polyvinyl alcohol-based column filler is used, thereby accomplishing the present invention.

For a mixed solvent to be used as a moving phase, a mixed solvent containing TFA at a concentration of 3 to 10%, preferably 5 to 10%, and most preferably 7 to 10%, by volume, is exemplified. For a solvent to be used as the mixed solvent, compatible, flowable or fluid, halogenated hydrocarbons i.e. chlorinated hydrocarbons, such as dichloromethane, chloroform and 1,2-dichloroethane are preferably used. If amino acids having thiol group, such as cysteine, in the peptide, β-mercaptoethanol or the like may be added as an antioxidant for thiol group. The quantity of β-mercaptoethanol to be added is adequately 0.1 mM as the final concentration.

According to the purification method of the present invention, it is additionally possible to purify a wide range of the other hydrophobic polypeptides as well as the other hydrophobic lipoprotein (ex. SP-B) contained in pulmonary surfactant.

BEST MODE FOR CARRYING OUT THE INVENTION

Now, the present invention is further explained with referring to the examples.

In the examples, 0.05 to 5 mg of crude polypeptide with sequence number 1 synthesized according to solid-phase method was subjected to HPLC for 75 min. using Asahipak GS-510 (diameter 7.5×500 mm) column (trademark, Asahi Kasei Co. Ltd.) and at a flow rate of 0.8 ml/min.

The result of the purification was evaluated from the color of the polypeptide obtained and the value of the surface activity of the pulmonary surfactant prepared from said polypeptide.

For determining the color of the polypeptide, TFA solution was prepared.

The preparation of pulmonary surfactant was carried out according to the following procedure. To each of purified polypeptide solution in TFA (12 mg/0.5 ml) was added 100 ml of chloroform-methanol solution (2:1, v/v) containing 1,2-dipalmitoylglycero-(3)-phosphocholine (660 mg), 1,2-diacyl-sn-glycero-(3)-phospho-sn-glycerol (220 mg) and palmitic acid(100 mg) and the mixture obtained was then dried and solidified under reduced pressure. The residue obtained was suspended in 100 ml of H$_2$O-ethanol mixture (9:1, v/v) at a temperature of 40° C. and spending 15 min., then lyophilized for 36 hours at −50° C. and a vacuum degree of 85 to 100 µHg to prepare pulmonary surfactant.

The surface activity was evaluated from the measurement of the activity lowering surface tension, spreadability over a gas-liquid interface and adsorbability to a gas-liquid interface.

REFERENCE EXAMPLE 1

10 mg of polypeptide of sequence number 1 (hydrophobic amino acid content: 81.4%) was dissolved in formic acid, and methanol-H$_2$O solution (70:30, v/v) containing 10 mM β-mercaptoethanol which is a solvent to be used as a moving phase was then added thereto to prepare a sample solution at a concentration of 2 mg/ml.

100 µl of the sample solution was injected into a column equilibrated with the aforementioned moving phase and subjected to HPLC in said moving phase. The detection was carried out at 250 nm, and the sample solution was divided into 15 fractions. Each fraction was then dried and solidified under reduced pressure, and the dry weight thereof was measured. From each purified polypeptide, pulmonary surface was prepared, and the surface activity thereof was determined.

The polypeptide obtained appears yellowish when it is dissolved in TFA. Yield of active fraction was 37%.

Activity lowering surface tension: Maximum surface tension 33.8 dyne/cm Minimum surface tension 4.1 dyne/cm Spreadabiliy over a gas-liquid interface: Reaching time 60 seconds Equilibrated surface tension 4.1 dyne/cm Adsorbability to a gas-liquid interface: Reaching time 90 seconds Equilibrated surface tension 32.6 dyne/cm (The results of the measurement are the ones of fractions which showed the most excellent activity. The same was applied to the following.)

EXAMPLE 1

20 mg of polypeptide of sequence number 1 was dissolved in 1 ml of TFA. The resulting solution was processed according to the procedure as described in the Reference Example 1 except TFA-dichloromethane solution (10:90, v/v) containing 10 mM of β-mercaptoethanol was used as the moving phase.

The polypeptide obtained has no color when it is dissolved in TFA and the yield of the active fraction was 66%.

The value of surface activity of the pulmonary surfactant containing this polypeptide is as follows.

Activity lowering surface tension: Maximum surface tension 29.5 dyne/cm Minimum surface tension 2.7 dyne/cm Spreadabiliy over a gas-liquid interface: Reaching time 30 seconds Equilibrated surface tension 29.4 dyne/cm Adsorbability to a gas-liquid interface: Reaching time 40 seconds Equilibrated surface tension 30.1 dyne/cm

EXAMPLE 2

20 mg of polypeptide (content of hydrophobic amino acid: 81.4%) of sequence number 1 was dissolved in 1 ml of TFA. The resulting solution was processed according to the procedure as described in the Example 1 except TFA-dichloromethane solution (3:97, v/v) was used as the moving phase.

The polypeptide obtained has no color when it is dissolved in TFA and the yield of the active fraction was 42%.

The value of surface activity of the pulmonary surfactant containing this polypeptide is as follows.

Activity lowering surface tension: Maximum surface tension 28.9 dyne/cm Minimum surface tension 2.1 dyne/cm Spreadabiliy over a gas-liquid interface: Reaching time 40 seconds Equilibrated surface tension 29.0 dyne/cm Adsorbability to a gas-liquid interface: Reaching time 50 seconds Equilibrated surface tension 31.4 dyne/cm

EXAMPLE 3

Polypeptide of sequence number of 11 was purified according to the procedure as described in Example 2. It is observed that TFA solutions of the polypeptide obtained has no color.

What is claimed is:

1. Method of purification of hydrophobic polypeptide comprising effecting the purification by high performance liquid chromatography using a mixed solvent as moving phase having from 3 to 10% by volume of trifluoroacetic acid, and polyvinyl alcohol-based column filler.

2. Method of claim 1 wherein the moving phase has 5 to 10% by volume of trifluoroacetic acid.

3. Method of claim 1 wherein the moving phase has 7 to 10% by volume of trifluoroacetic acid.

4. Method of claim 1 wherein the hydrophobic polypeptide is one which can demonstrate a surface active property by combining it with a lipid mixture.

5. Method of claim 1 wherein the hydrophobic polypeptide is a polypeptide defined by a sequence ID number from 1 to 11.

6. Method of claim 4 wherein the hydrophobic polypeptide is a polypeptide defined by a sequence ID number from 1 to 11.

7. Method of purification of hydrophobic polypeptide comprising effecting the purification by high performance liquid chromatography using a mixed solvent as moving phase having from 3 to 10% by volume of trifluoroacetic acid, and polyvinyl alcohol-based column filler, wherein the mixed solvent is composed of trifluoroacetic acid and a compatible, flowable halogenated hydrocarbon.

8. Method of claim 7 wherein the moving phase has 5 to 10% by volume of trifluoroacetic acid.

9. Method of claim 7 wherein the moving phase has 7 to 10% by volume of trifluoroacetic acid.

10. Method of claim 7 wherein the mixed solvent further contains β-mercaptoethanol.

11. Method of claim 7 wherein the halogenated hydrocarbon is chlorinated hydrocarbon.

12. Method of claim 7 wherein the halogenated hydrocarbon is selected from the group consisting of dichloromethane, chloroform and dichloroethane.

13. Method of claim 7 wherein the hydrophobic polypeptide is one which can demonstrate a surface active property by combining it with a lipid mixture.

14. Method of claim 7 wherein the hydrophobic polypeptide is a polypeptide defined by a sequence ID number from 1 to 11.

15. Method of claim 13 wherein the hydrophobic polypeptide is a polypeptide defined by a sequence ID number from 1 to 11.

16. Method of purification of hydrophobic polypeptide comprising effecting the purification by high performance liquid chromatography using a mixed solvent as moving phase having from 3 to 10% by volume of trifluoroacetic acid, and polyvinyl alcohol-based column filler, wherein the hydrophobic polypeptide has a hydrophobic amino acid content of more than 50%.

17. Method of claim 16 wherein the moving phase has 5 to 10% by volume of trifluoroacetic acid.

18. Method of claim 16 wherein the moving phase has 7 to 10% by volume of trifluoroacetic acid.

19. Method of claim 16 wherein the hydrophobic polypeptide is one which can demonstrate a surface active property by combining it with a lipid mixture.

20. Method of claim 16 wherein the hydrophobic polypeptide is a polypeptide defined by a sequence ID number from 1 to 11.

21. Method of claim 19 wherein the hydrophobic polypeptide is a polypeptide defined by a sequence ID number from 1 to 11.

22. Method of claim 16 wherein the mixed solvent is composed of trifluoroacetic acid and a compatible, flowable halogenated hydrocarbon.

23. Method of claim 22 wherein the mixed solvent further contains β-mercaptoethanol.

24. Method of claim 22 wherein the halogenated hydrocarbon is chlorinated hydrocarbon.

25. Method of claim 22 wherein the halogenated hydrocarbon is selected from the group consisting of dichloromethane, chloroform and dichloroethane.

26. Method of claim 22 wherein the hydrophobic polypeptide is one which can demonstrate a surface active property by combining it with a lipid mixture.

27. Method of claim 22 wherein the hydrophobic polypeptide is a polypeptide defined by a sequence ID number from 1 to 11.

28. Method of claim 26 wherein the hydrophobic polypeptide is a polypeptide defined by a sequence ID number from 1 to 11.

* * * * *